US006760610B2

(12) United States Patent
Tschupp et al.

(10) Patent No.: US 6,760,610 B2
(45) Date of Patent: Jul. 6, 2004

(54) SENSOR AND METHOD FOR MEASUREMENT OF PHYSIOLOGICAL PARAMETERS

(75) Inventors: Andreas Tschupp, Therwil (CH); Matthias Roost, Doerfingen (CH); Joseph Lang, Ranspach le haut (FR)

(73) Assignee: Sentec AG, Therwil (CH)

( * ) Notice: Subject to any disclaimer, the term of this patent is extended or adjusted under 35 U.S.C. 154(b) by 169 days.

(21) Appl. No.: 09/766,541

(22) Filed: Jan. 18, 2001

(65) Prior Publication Data

US 2002/0062070 A1 May 23, 2002

(30) Foreign Application Priority Data

Nov. 23, 2000 (CH) .............................. PCT/CH00/00628

(51) Int. Cl.[7] ................................................. A61B 5/05
(52) U.S. Cl. .................... 600/345; 600/309; 600/354; 600/357; 600/509
(58) Field of Search ................................ 600/345, 309, 600/347, 348, 353, 354, 355, 357, 358, 359, 508, 509; 128/903, 904

(56) References Cited

U.S. PATENT DOCUMENTS

| | | | |
|---|---|---|---|
| 4,129,125 A | 12/1978 | Lester et al. | |
| 4,840,179 A | 6/1989 | Ulrich | |
| 5,259,381 A | 11/1993 | Cheung et al. | |
| 5,342,498 A | 8/1994 | Graves et al. | |
| 5,673,692 A | 10/1997 | Schulze et al. | |
| 5,749,365 A | 5/1998 | Magill | |
| 5,803,908 A | 9/1998 | Steuer et al. | |
| 5,862,803 A | 1/1999 | Besson et al. | |
| 5,873,821 A | 2/1999 | Chance et al. | |
| 5,957,854 A | * 9/1999 | Besson et al. | ............... 600/509 |
| 6,144,869 A | * 11/2000 | Berner et al. | ............... 600/347 |
| 6,233,471 B1 | * 5/2001 | Berner et al. | ............... 600/345 |
| 6,272,364 B1 | * 8/2001 | Kurnik | ................. 600/345 |
| 6,289,238 B1 | * 9/2001 | Besson et al. | ............... 600/509 |
| 6,299,578 B1 | * 10/2001 | Kurnik et al. | ............... 600/309 |
| 6,309,351 B1 | * 10/2001 | Kurnik et al. | ............... 600/309 |
| 6,356,776 B1 | * 3/2002 | Berner et al. | ............... 600/347 |

FOREIGN PATENT DOCUMENTS

| | | |
|---|---|---|
| CA | 2920083 | 5/2001 |
| CH | 690 081 | 4/2000 |
| EP | 0 267 978 | 5/1988 |
| EP | 0770349 A1 | 5/1997 |
| WO | WO 99/13765 A1 | 3/1999 |
| WO | WO 00/42911 | 7/2000 |
| WO | WO 00/53082 | 9/2000 |

OTHER PUBLICATIONS

"Noninvasive Assessment of Blood, Gases, State of the Art", J. S. Clark, et al., Am. Rev. Resp. Dis., vol. 145, 1992, pp. 220–232.

"Can Pulse Oximetry Be Used To Measure Systolic Blood Pressure", R. Chawla, et al., Anesth Analg, 1992; 74:196–200.

International Search Report of PCT/CH 01/00685, dated May 2, 2002.

Sentec Product Literature dated Jun. 2003.

* cited by examiner

Primary Examiner—Teresa Walberg
Assistant Examiner—Fadi H. Dahbour
(74) Attorney, Agent, or Firm—Eitan, Pearl, Latzer & Cohen Zedek, LLP

(57) ABSTRACT

A sensor for the measurement of physiological parameters in the blood, including at least one measuring apparatus and a digital sensor signal processor which is arranged in the sensor, and which is connected in a signal conducting manner to the measuring apparatus. The sensor may output a digital output signal, which may be transmitted to a signal evaluation device using a connection cable.

41 Claims, 5 Drawing Sheets

Figure 1:
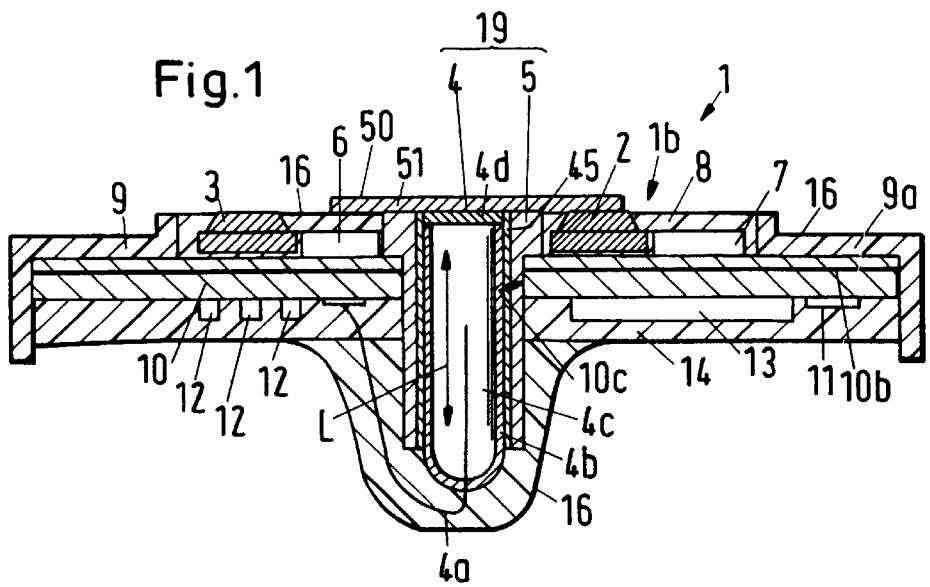

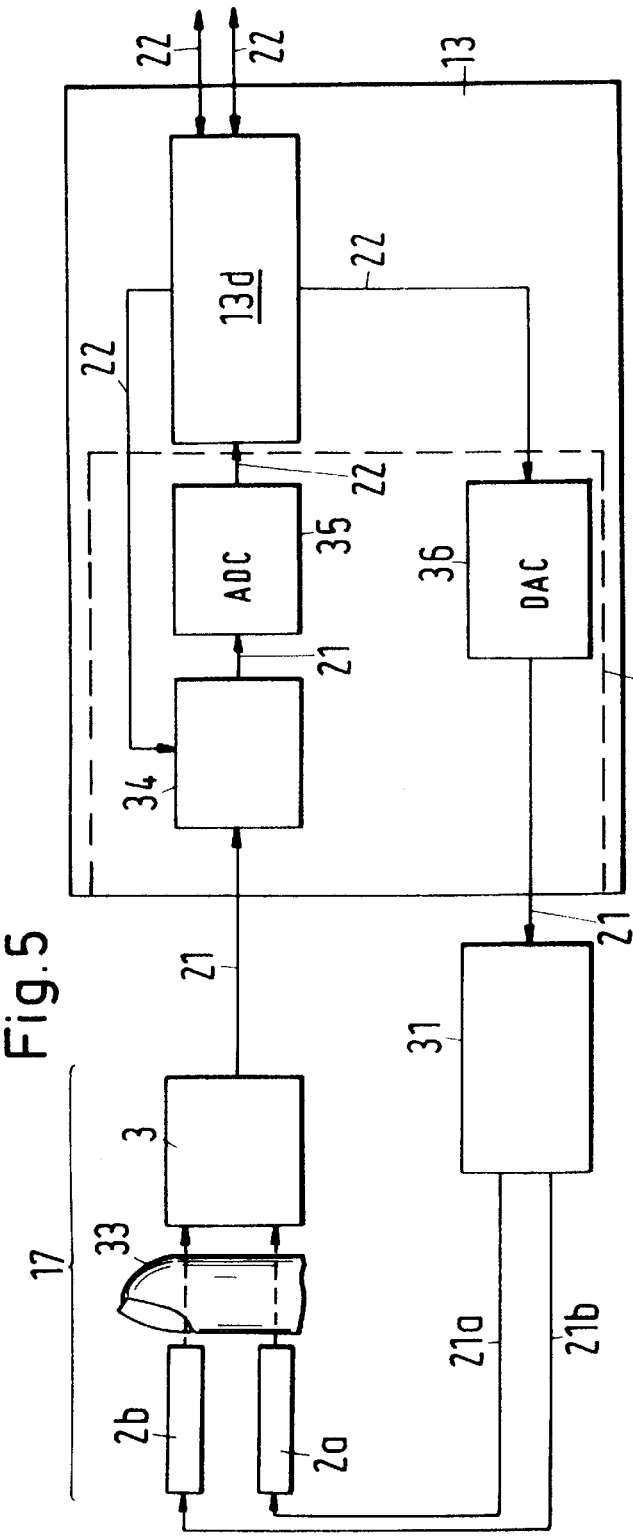
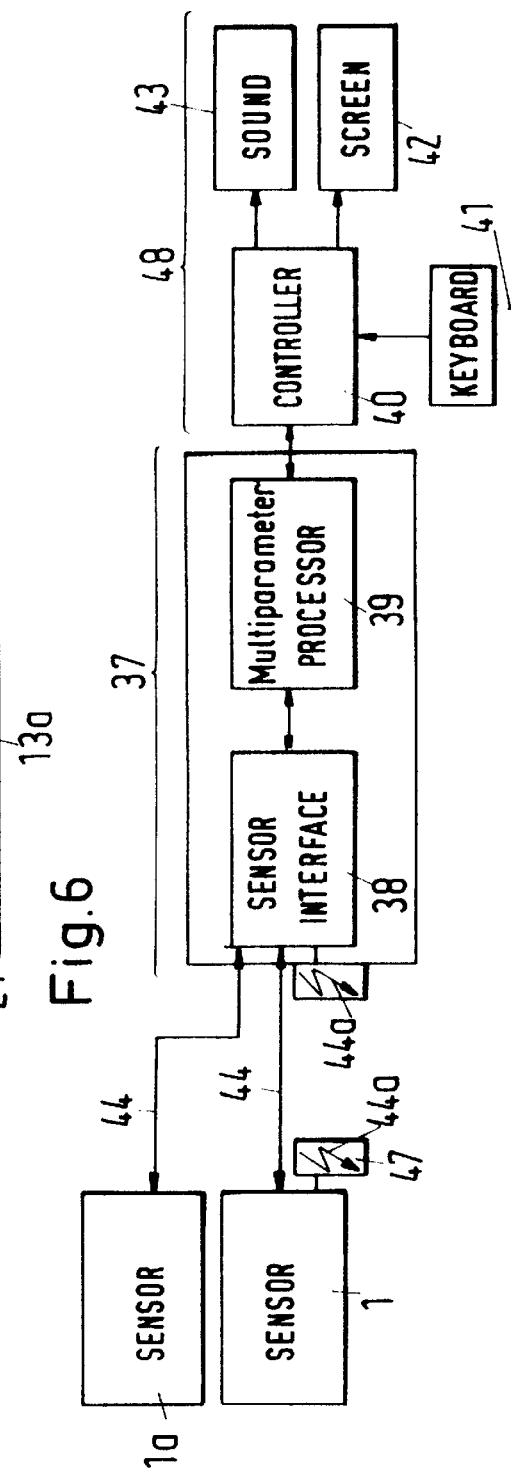

SENSOR AND METHOD FOR MEASUREMENT OF PHYSIOLOGICAL PARAMETERS

CROSS REFERENCE TO RELATED APPLICATIONS

This application claims the benefit of PCT Application CH00/00628, entitled "SENSOR AND METHOD FOR MEASUREMENT OF PHYSIOLOGICAL PARAMETERS", filed Nov. 23, 2000.

FIELD OF THE INVENTION

The invention relates to a sensor for the measurement of physiological parameters. The invention relates further to a method for the measurement of physiological parameters.

BACKGROUND OF THE INVENTION

The measurement of one or more physiological parameters of the human body is increasingly gaining in significance. Thus, a combination sensor for the combined measurement of the oxygen saturation of the haemoglobin in arterial blood and also of the arterial partial pressure of carbon dioxide is known from the document EP 0 267 978 A1. For the measurement of the oxygen saturation ($SpO_2$) a non-invasive, optical, and generally known method is used which is termed pulse oximetry. A pulse oximeter system of this kind comprises a sensor which is applied to a location of the human body with a good blood supply, a pulse oximeter, and also a connection cable which connects the sensor to the pulse oximeter. For the measurement of the $CO_2$ concentration in the blood, the transcutaneous carbon dioxide partial pressure ($tcpCO_2$) is determined with the aid of an electrochemical measuring apparatus. Detailed information concerning these generally known measurement methods are, for example, to be found in the following review article: "Noninvasive Assessment of Blood Gases, State of the Art" by J. S. Clark et al., Am. Rev. Resp. Dis., Vol. 145, 1992, pages 220–232. Details of the pulse oximetry measurement method are for example to be found in the document WO 00/42911.

Disadvantages of the sensor disclosed in the document EP 0 267 978 A1 are the facts that disturbing signals which arise falsify the measurement, that the sensor has to be calibrated frequently, that the sensor has a relatively thick cable, that the sensor together with the evaluation device is relatively expensive, and that the sensor only permits relatively simple measurements to be carried out.

SUMMARY OF THE INVENTION

According to some embodiments of the present invention a sensor is provided that may include at least one measuring apparatus and also a digital sensor signal processor which is arranged in the sensor and which is connected in a signal conducting manner to the measuring apparatus and which makes available a digital output signal. According to some embodiments of the present invention, a method may be provided for the measurement of physiological parameters in which an analog measured value of a measuring apparatus is detected by a sensor, the analog measured value is converted into digital values in the sensor and the digital values are supplied to a signal evaluation device.

The object is in particular satisfied by a sensor for the measurement of physiological parameters such as oxygen or carbon dioxide in the blood comprising at least one measuring apparatus and also a digital sensor signal processor arranged in the sensor which is connected in signal-conducting manner to the measuring apparatus and which makes the measured values available in digital form for the further processing.

The sensor of the invention has a digital sensor signal processor which digitises the signal measured by the measuring apparatus, so that this signal is available in the sensor for further processing in digital form. A digital sensor signal processor of this kind is also referred to in English as DSSP (Digital Sensor Signal Processor) or as Single Chip MCU (MiroComputerUnit). A sensor signal processor of this kind comprises not only a microcontroller with memory, microprocessor and interfaces on a single chip, but rather also an analog-to-digital converter and also a digital-to-analog converter. The digital sensor signal processor enables, amongst other things, the values measured by the measuring apparatuses arranged in the sensor to be converted into digital values within the sensor. From this, the following advantages arise in particular:

The measured, analog signal is converted within the sensor into a digital signal which is insensitive to disturbance. This also permits weak analog signals to be measured cleanly.

The signal is digitally transmitted between the sensor and a subsequent evaluation device, which extensively precludes signal falsification due to stray radiation.

The evaluation device can be arranged within the sensor or spaced apart from the sensor.

Two conductive wires are sufficient for the transmission of the digital data. The connection cable between the sensor and the evaluation device can thus be made very thin.

A digital signal processing is essentially carried out in the evaluation device. This enables a favourably priced evaluation device obtainable as a standard product, with a processor and matched software corresponding to the sensor.

In an advantageous design of the sensor, the data transmission takes place in cableless manner between the sensor and the evaluation device, for example by means of electromagnetic waves.

In a further advantageous embodiment the sensor is designed such that its digital output signals have fixed normalised values. In a preferred embodiment a reference curve, for example a calibration curve of the measuring apparatus arranged in the sensor is stored in the sensor. Such sensors have the advantage that no time-consuming or costly calibration is required on changing the sensor, since all sensors have a specified output signal.

In a further advantageous embodiment the sensor has a circuit board which is equipped with the essential or all required electronic components. A sensor of this kind can be manufactured at extremely favourite cost.

In a further advantageous embodiment the sensor has an inner space which is electrically screened against the outside, which yields the advantage that disturbing signals cannot or can hardly be superimposed on the measured signals.

It is of central importance that the sensor of the invention also allows weak signals to be measured unambiguously and that the measured signals can be supplied free of disturbance to a signal evaluation device. This has the consequence that no complicated method is required for the signal evaluation in order to unambiguously and reproducibly evaluate an otherwise normally noisy signal.

It has proved to be particularly advantageous to use the sensor of the invention on the ear, in particular on the earlobe. Moreover, it is particularly advantageous to heat the sensor with a heating device in order to thereby keep the earlobe at a reproducibly constant temperature. The earlobe proves to be a particularly advantageous measurement position, because the ear is located relatively close to the heart with respect to the blood circulation, substantially closer than the finger cap, which is, for example, also suitable for the measurement of oxygen or carbon dioxide in the blood. Moreover, as a result of the heating, hardly any vascular construction or hardly any vessel narrowing arises at the ear by reason of the heating. The sensor of the invention thus enables measurement to be made at the earlobe with a very low Signal to Noise (S/N) ratio, so that a measurement signal of excellent quality is available.

This high signal quality now in turn enables further physiological parameters to be determined from the measured values, such as, for example, the blood pressure, which is measured by means of the so-called CNIBP method, which signifies in English "Continuous NonInvasive Blood Pressure". In this connection the systolic blood pressure is, for example, determined by means of the pulse oximetric measurement method which can be measured at the earlobe, as is for example described in detail in the following document: "Can Pulse Oximetry Be Used to Measure Systolic Blood Pressure?, R. Chawla et al., Anesth Analg, 1992; 74:196–200". The sensor of the invention permits the pulse curve shape, for example the so-called plethysmogram to be measured in that the oxygen content of the blood is measured pulse oximetrically for example 50 or 100 times per second and the blood pressure is determined from the resulting shape of the curve.

The high signal quality enables the hemotacrit, abbreviated internationally with "HCT" to be determined as a further physiological parameter. The determination of this parameter is, for example, disclosed in detail in the document U.S. Pat. No. 5,803,908.

The sensor in accordance with the invention is also suitable for the measurement of the composition of the respiratory air.

In a further advantageous embodiment a data memory is arranged in the sensor in which measured values or patient data can for example be stored. In an advantageous embodiment this data memory is made sufficiently large that data measured over a longer period of time can be stored in the sensor, for example in a nonvolatile memory, also termed an EEPROM.

In an advantageous method, the measured values are supplied to a signal evaluation device arranged after the sensor and the evaluated data are supplied at least partly to the sensor again and stored in its nonvolatile memory. The sensor can also be connected to different signal evaluation devices temporally one after the other, which respectively store the evaluated data in the memory of the sensor. A signal evaluation device can, if required, also access the data stored in the memory, for example the patient data.

The sensor in accordance with the invention is, for example, also suitable for the longer term monitoring of patients, for example also in emergency situations, in which the sensor is, for example, secured to the patient's ear and the sensor remains continually with the patient and the data of the signal evaluation devices, to which the sensor is respectively connected one after the other, is at least partly stored. Thus, it is possible with a single sensor to continuously monitor a patient substantially without gaps, starting for example at the site of an accident, and subsequently in the ambulance, in the operating theatre through to the wake-up station. Thanks to the fact that all the measurement data is available at every station and, moreover, that even further patient data is eventually available, reliable data is also available at any time in emergency situations, which enables an ideal care of a patient.

DETAILED DESCRIPTION OF THE DRAWINGS

Figure 2:
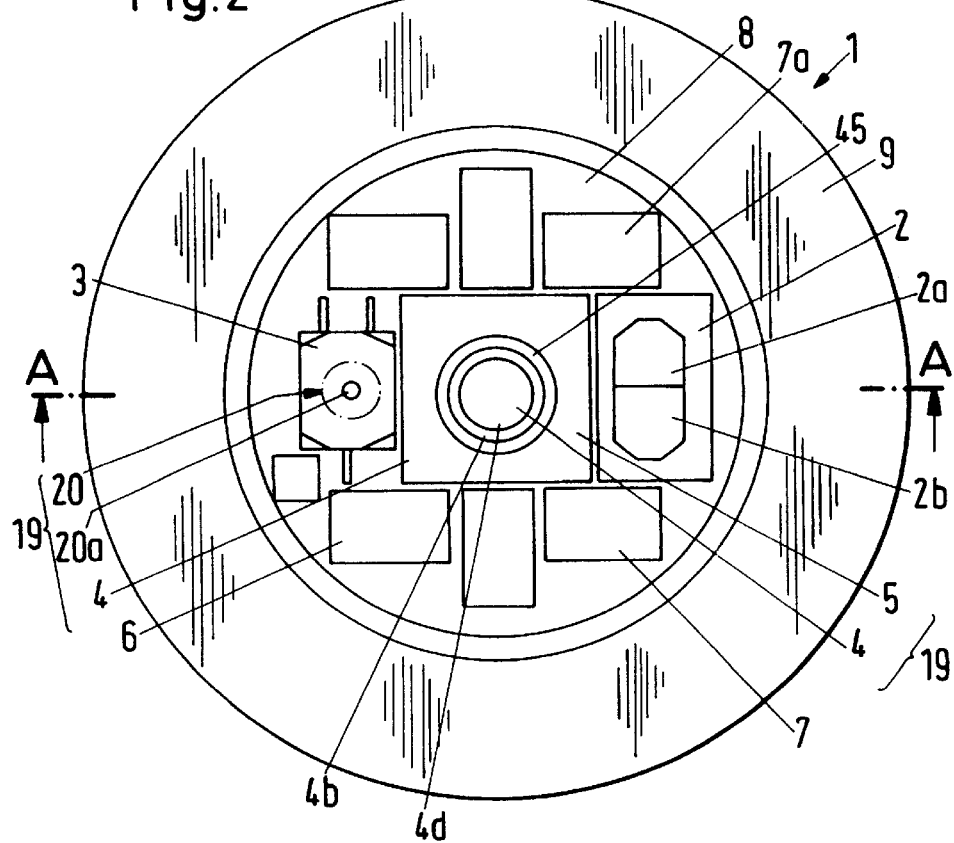
Figure 3:
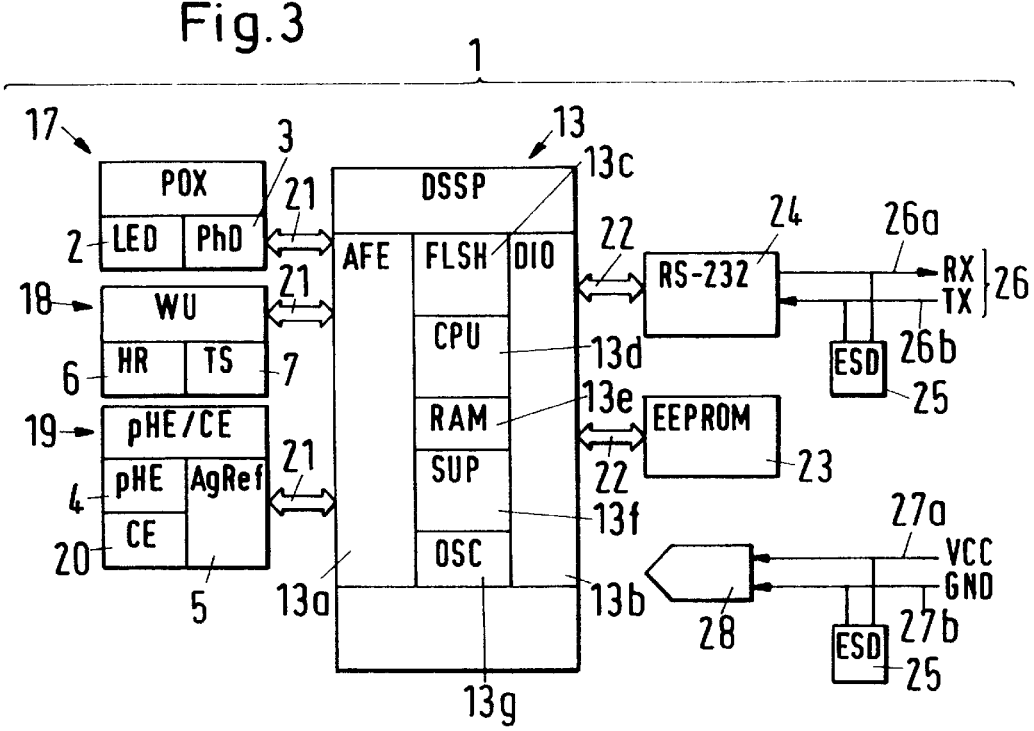
Figure 4:
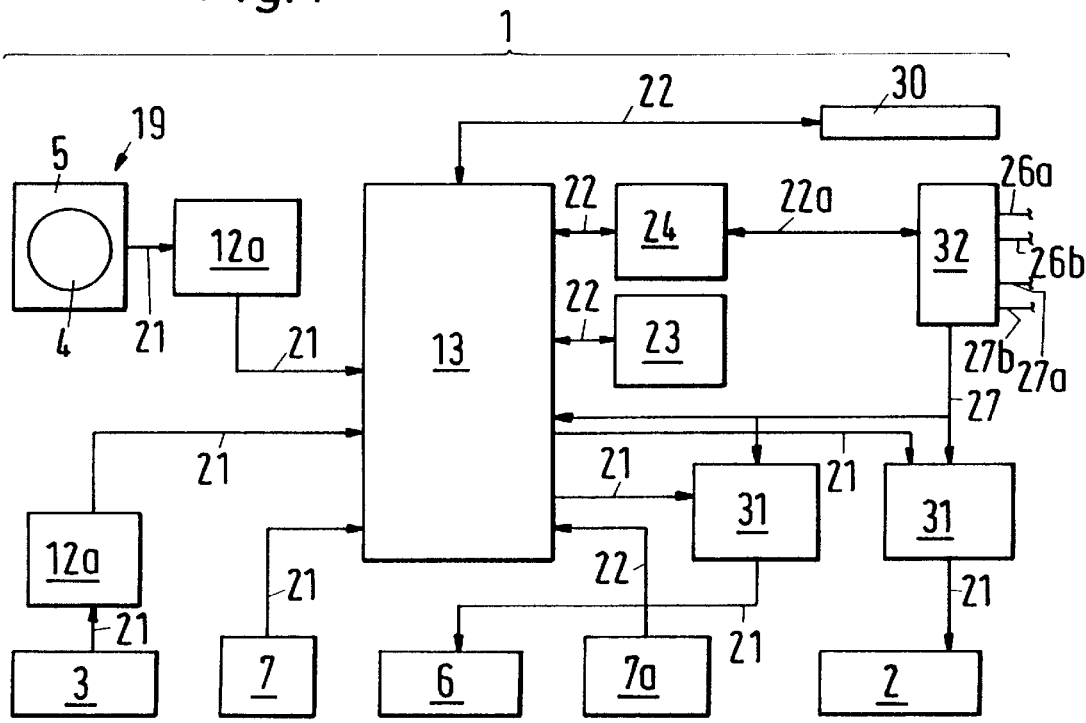
Figure 7:
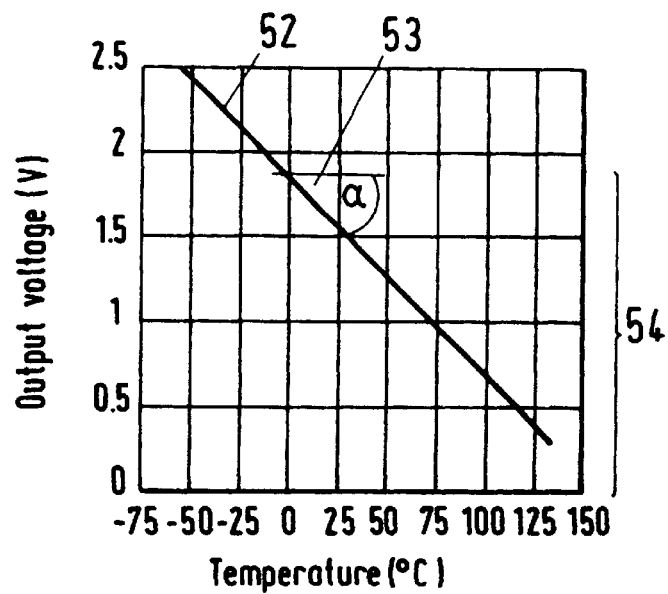
Figure 8:
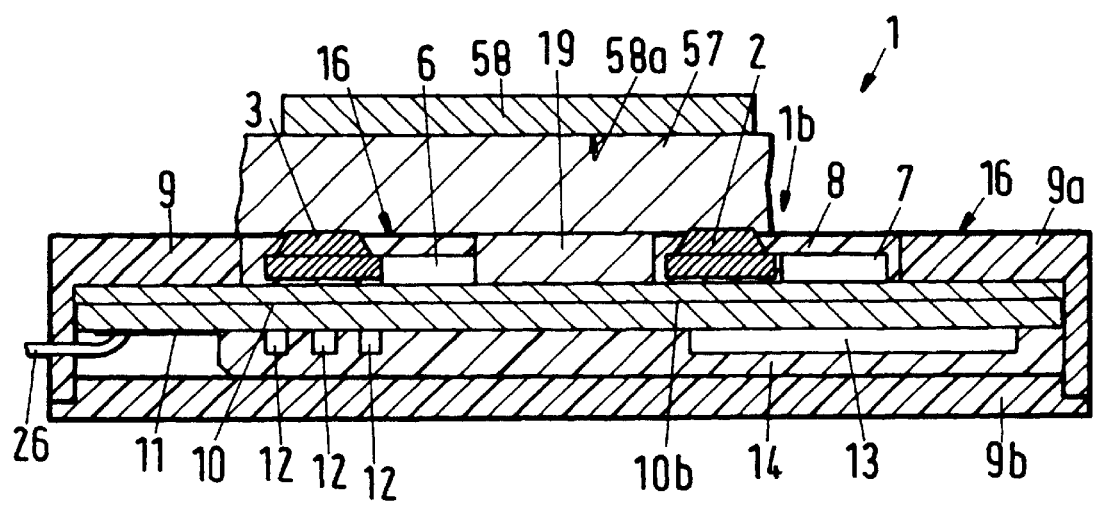
Figure 9:
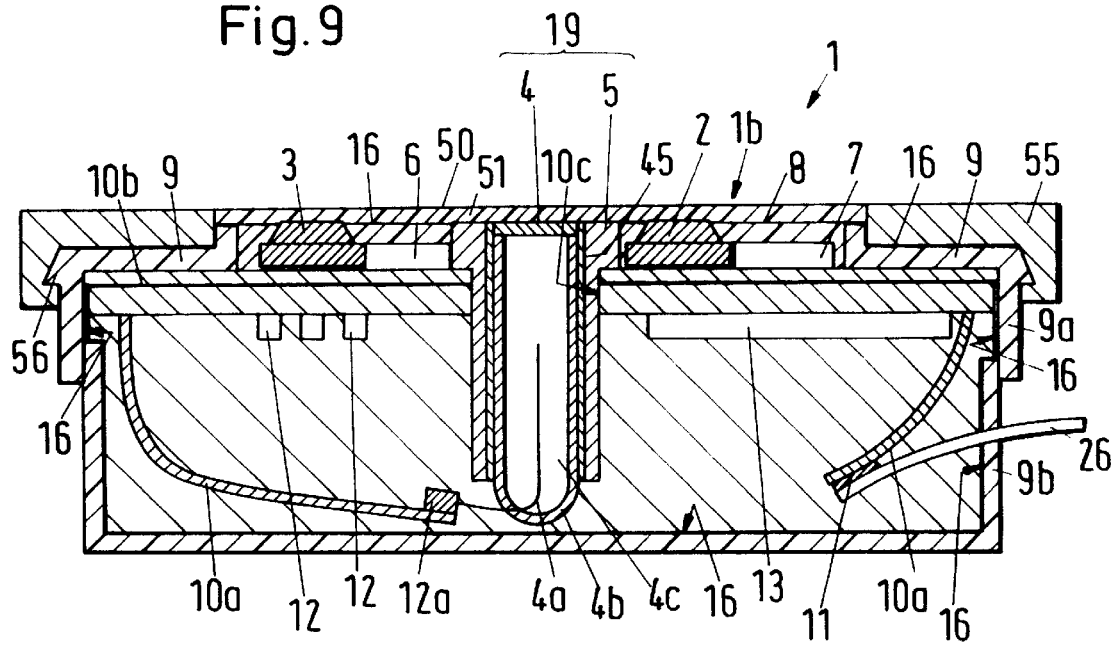
Figure 10:
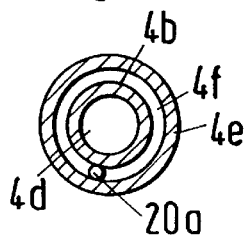
Figure 11:
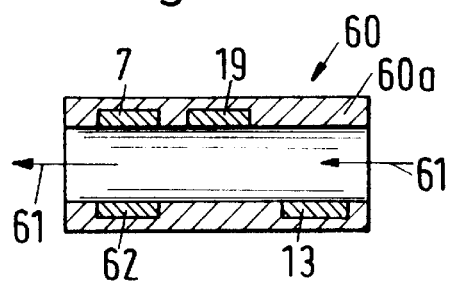
Figure 12:
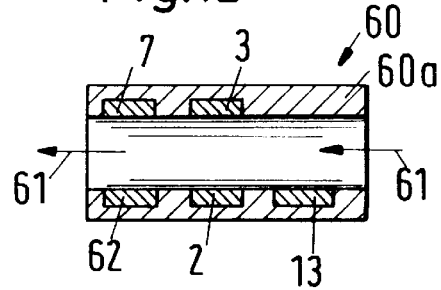

The invention will be described in the following with reference to embodiments in which are shown:

FIG. 1 a longitudinal section through a sensor in accordance with the invention;

FIG. 2 a plan view of a sensor;

FIG. 3 schematically, a block diagram of the sensor;

FIG. 4 schematically, a further block diagram of a sensor;

FIG. 5 a detail aspect of the sensor signal processor;

FIG. 6 a plurality of sensors connected to a signal evaluation device;

FIG. 7 a correction curve for a measurement apparatus;

FIG. 8 a longitudinal section through a further sensor in accordance with the invention which contacts an earlobe;

FIG. 9 a longitudinal section through a further sensor in accordance with the invention;

FIG. 10 a cross-section through a micro-pH-electrode;

FIG. 11 a longitudinal section through a respiratory gas measuring apparatus;

FIG. 12 a longitudinal section through a further respiratory gas measuring apparatus;

DETAILED DESCRIPTION OF THE INVENTION

In the following the same reference numerals are used for the same items.

The sensor shown in FIG. 1 permits a combined measurement of the arterial oxygen saturation ($SpO_2$) and of the transcutaneous $CO_2$ partial pressure ($tcpCO_2$). For the measurement of the oxygen saturation the sensor 1 has a pulse oximetric measurement system 17 which includes a two-colour light emitting diode 2 (LED) and also a photodetector 3. The two-colour light emitting diode 2 comprises two light emitting diodes 2a, 2b arranged alongside one another in a common housing, with the one light emitting diode 2a having a wavelength of approximately 660 nm (red) and the other light emitting diode 2b having a wavelength of 890 nm (infrared). The sensor 1 has a surface 1b over which a membrane 50 is arranged in the illustrated embodiment with a thin layer electrolyte 51 therebetween. This membrane 50 is applied to the skin at a point of the human body well supplied with blood, for example at a finger or at the earlobe. The light emitted from the two light emitting diodes 2a, 2b shines through the electrolyte 51 located between the light emitting diodes 2a, 2b and also the membrane 50 and is directed into the non-illustrated body part which is well supplied with blood and is scattered there and partly absorbed. The light reflected by the body part is measured by the photodetector 3. The signal measured by the photodetector 3 is supplied to a digital sensor signal processor 13 designated in abbreviated from also as DSSP.

The illustrated sensor 1 moreover comprises an electrochemical measuring apparatus 19 for the measurement of the transcutaneous carbon dioxide partial pressure $tcpCO_2$ measurement, with this measuring apparatus 19 including a micro-pH-electrode 4 and also an Ag/AgCl reference electrode 5. The transcutaneous carbon dioxide partial pressure is measured potentiometrically in that the pH value of the thin layer of the electrolyte solution 51 is measured, which communicates with the skin via the hydrophobic membrane 50 which is readily permeable to gas. A change of the $pCO_2$ value at the skin surface causes a pH change of the electrolyte solution which behaves proportional to the logarithm of the $pCO_2$ change. The pH value is measured in that the potential between the miniature pH electrode 4 and the Ag/AgCl reference electrode 5 is measured. The micro-pH-electrode 4 is connected in signal conducting manner to the digital sensor signal processor 13 via the inner electrical conductor 4a.

The illustrated sensor 1 includes moreover a heating system 18 comprising a heating-up device formed as an electrical resistance and also a temperature sensor 7 for the temperature regulation. The heating system 18 is advantageously used in combination with the electrochemical measuring apparatus 19 in order to heat up the underlying skin via the sensor surface 1b. For the transcutaneous measurement of the carbon dioxide partial pressure $pCO_2$ or of the oxygen partial pressure $pO_2$, the sensor surface 1b is for example heated up to a temperature of about 40° C. to 45° C.

The sensor 1 includes a multilayer rigid circuit board 10 which is equipped with electronic components 2, 3, 6, 7, 12, 13 and which has a plurality of non-illustrated electrically conductive tracks in order to connect the electronic components such as the light emitting diode 2, the photodetector 3, the resistor 6, the temperature sensor 7, a second temperature sensor 7a or further electronic components, such as amplifiers 12, 12a in a signal conducting manner, in particular to the digital sensor signal processor 13. All electronic components are formed using SMD technology (Surface Mounted Device) which results in the advantage that the circuit board 10 can be automatically equipped and can thus be manufactured at very favourable cost. At the centre of the circular circuit board 10 an opening 10c is cut out in the form of a round hole in which the electrochemical measuring apparatus 19 comprising the micro-pH-electrode 4 and also the Ag/AgCl reference electrode 5 is arranged. The micro-pH-electrode 4 is formed as a glass electrode and has an inner electrolyte 4c which is surrounded by a shaft glass 4b and also a membrane glass 4d. The potential arising in the inner electrolyte 4c is supplied via the inner conductor 4a to an amplifier 12. An insulator 45 is arranged by between the micro-pH-electrode 4 and the reference electrode 5.

Within the circuit board 10 a substantially full area, electrically conductive layer 10b is arranged which serves for the screening of electrical fields. Many non-illustrated conductor tracks extend in insulated manner and transversely through the electrically conductive layer 10b in order to connect electronic components arranged on the circuit board 10 above and below it. The layer 10b is of full area design, with the exception of the apertures caused by the transversely extending conductive tracks.

The heat sensitive electrode 4 is adhered by an electrically conductive epoxy resin to the circuit board 10, with this adhesive being arranged such that an electrically conductive connection is formed between the layer 10b opening at the aperture 10c and the Ag/AgCl reference electrode 5. The reference electrode 5 is thus connected to the and forms moreover a screen against electrical fields.

The circuit board 10 is contained in a housing 9. The housing 9 consists of a plastic body provided with an electrically conductive surface, such as a metal layer. The electronic components arranged above the circuit board 10 are surrounded by a heat conducting cover 8 which is preferably designed as a heat conducting potting. The space between the surface of the circuit board 10 and the sensor surface 1b is preferably potted with a heat conducting, electrically insulating epoxy resin. The sensor surface 1b is processed such that the components light emitting diode 2, photodetector 3 and the electrochemical measuring apparatus 19 and the heat conducting potting 8 which open at the surface form a planar surface. The heat conducting potting 8 has the advantage that the heat produced by the resistor 6 can be transferred with low loss and uniformly distributed to the sensor surface 1b, so that the skin which contacts the membrane 50 during the measurement can be uniformly warmed.

The electronic components 12, 13 arranged beneath the circuit board 10 are surrounded by an electrically insulating cover 14, 15. For this cover 14, 15 an epoxy resin, and preferably an electrically highly insulating epoxy resin is used which is cast in place. The inner conductor 4a extending from the electrode 4 to the circuit board 10 is embedded in the highly insulating epoxy resin in order to largely suppress disturbing electrical influences.

The cover 14, 15, the housing 9, and also parts of the heat conducting cover 8 are surrounded by a metallic cover 16 in order to protect the interior of the sensor 1 from disturbing electrical and electromagnetic influences. The metallic layer 10b providing blanket coverage within the circuit board 10 or arranged at its surface is not absolutely essential, but has, amongst other things, the advantage that it prevents the propagation of disturbing electromagnetic influences produced within the sensor 1, since the electronic components 2, 3, 6, 7 arranged above the circuit board 10 are screened from the electronic components 12, 13 arranged beneath the circuit board. The electronic components 2, 3, 6, 7, 12, 13 are moreover arranged distributed in the sensor 1 such that they exert as far as possible no mutually disturbing influences. As can be seen from the section of FIG. 1 the high ohmic, and thus disturbance sensitive, inner conductor 4a is led extending to the left to an amplifier 12, whereas the digital sensor signal processor 13 is arranged at the right-hand side. These components are thus spatially separated, with the grounded reference electrode 5 located between them for additional screening. The digitally operating digital sensor signal processor 13 is thus screened from the remaining electronic components 2, 3, 6, 7, 12 which operate in analog manner. The sensor 1 with components and screens arranged in this way enables a signal processing with an extremely low interference signal component.

The electrode 4 is of elongate design and has a longitudinal direction L. The circuit board 10 extends perpendicular to the longitudinal direction L and is arranged within the length of the electrode 4. This arrangement of the circuit board 10 with the respective electrode 4 has the advantage that the light emitting diode 2, the photodetector 3 and the heating device 6 come to lie close to the sensor surface 1b and that the electrical connection lines are very short. This arrangement has, amongst other things, the advantage of a low interference signal component.

The sensor 1 moreover includes electrical connections 11 which are connected in signal conducting manner to the sensor signal processor 13 to which a non-illustrated cable can be connected which supplies the electrical signals to a subsequent signal evaluation device 37. FIG. 1 shows essentially a section along the line A—A of FIG. 2.

A possible arrangement of the components described in FIG. 1 is shown in the view of the sensor surface 1b shown in FIG. 2. An insulator 45 is arranged between the micro-pH-electrode 4 and the reference electrode 5.

Moreover, a further electrochemical measuring apparatus 19 for the measurement of the transcutaneous oxygen partial pressure tcpO$_2$ could be arranged in the sensor 1. As FIG. 2 indicates the photodetector 3 could be replaced by an electrode 20 in accordance with Clark, which has a platinum wire 20a arranged at its centre. The electrode 20 forms, together with the Ag/AgCl reference electrode 5, the further electrochemical measuring apparatus 19 for the measurement of the oxygen partial pressure pO$_2$. In this measurement method, the light emitting diode 2 could be dispensed with. The platinum wire 20a could also be arranged extending within the photodetector 3 or the light emitting diode 2, with its end face opening at the surface. The platinum wire 20a could also be arranged, as can be seen in the section through the mirco-pH-electrode 4 shown in FIG. 10, between an outer shaft glass 4e and an inner shaft glass 4b, with the end of the platinum wire 20a opening to the surface of the membrane glass 4d.

Only a single measuring apparatus 17, 19 could also be arranged in the sensor 1. Measuring apparatuses for the measurement of the most diverse physiological parameters can also be arranged in the sensor 1. For example, a measuring apparatus known per se for the measurement of the core temperature Tk of the human body which permits the core temperature Tk to be determined by means of infrared radiation, i.e. with an infrared transmitter and infrared receiver, with the aid of a measurement at the timpanic membrane of the ear could be arranged in the sensor 1. Further measuring apparatuses known per se could also be arranged in the sensor 1, for example for the measurement of the hematocrit (HCT) of the blood pressure (CNIBP). One or also more such measuring apparatuses can in each case be arranged in the sensor 1.

FIG. 3 shows schematically, by way of a block diagram, the electronic components arranged in the sensor 1. Of particular importance is the digital sensor signal processor 13 arranged in the sensor 1 which enables an extensive digital signal processing in the sensor 1. A sensor signal processor of this kind, also termed in English "Digital Sensor Signal Processor" (DSSP) normally comprises:

- at least one analog input and output 13a (AFE) with at least one analog/digital converter 35 and at least one digital/analog converter 36,
- a digital input and output 13b (DIO),
- a nonvolatile memory 13c (FLSH),
- a central processor 13d (CPU),
- a working memory 13e (RAM).

The software for the control of the central processor 13d is stored in the nonvolatile memory 13c. This software determines how the individual components of the sensor signal processor and the measuring apparatuses 18, 19 are controlled and how the digital data are exchanged with a higher level signal evaluation device 37.

The sensor signal processor can include further components, such as for example an oscillator 13g (OSC) or a status monitoring device 13f (SUP), which resets the sensor signal processor 13 into a defined starting state, for example with a sudden failure.

The sensor signal processor 13 is connected via analog signal lines 21 with at least one of the measuring apparatuses 17, 18, 19. The optical measuring apparatus 17 comprises the light emitting diode 2 and the photodetector 3. The heating system 18 comprises the electrical resistor 6 and the temperature sensor 7. The electrochemical measuring apparatus 18 comprises the reference electrode 5 and the micro-pH-electrode 4 for the tcpCO$_2$ measurement in accordance with Stow-Severinghaus and/or the electrode 20 for the tcpO$_2$ measurement in accordance with Clark. The sensor 1 preferably comprises two temperature sensors, a digital temperature sensor 7 and also an analog temperature sensor 7a. In comparison to a sensor which operates in a purely analog manner, the substantially digital sensor of the invention has a substantially higher redundancy. Moreover, the state of the sensor can be monitored in a substantially more differentiated manner. Thus, it can, for example, be determined whether a digital signal is present or not. Conclusions can be drawn concerning the heating up of the sensor 1 from the total current consumed by it and, if necessary, the current supply or the heating power reduced. Through the use of two temperature sensors 7, their temperature can be compared at regular intervals and, if a greater deviation is present, it can be concluded that one of the temperatures sensors 7 is defective. The sensor 1 of the invention thus has the advantage that it operates substantially more reliably, that possible disturbances can be recognized early on and that temperatures in the sensor 1 which are too high, which could, for example, damage tissue such as the earlobe, are precluded.

The sensor signal processor 13 is connected via a digital input and output 13b and via a digital signal line 22 to a serial interface 24 also termed UART (Universal Asynchronous Receiver Transmitter) which enables via two serial conductors 26a, 26b a bidirectional exchange of data via a connection means 26 to the higher level signal evaluation device 37. In the illustrated embodiment the serial interface 24 is designed in accordance with the standard RS-232. An electrostatic dissipation device 25 (ESD) protects the serial interface 24 from over-voltages.

The sensor signal processor 13 can, moreover, be connected via digital signal line 22 to an additional memory 23, with the additional memory 23 preferably being formed as an EEPROM, which is referred to in English as "Electrical Erasable Programmable Read Only Memory". The individual components of the sensor 1 are supplied with electrical current via an energy supply 28. A feed voltage 27a (VCC) and also an ground 27b (GND) are supplied to the energy supply 28 via two conductors.

The block circuit diagram shown in FIG. 5 shows, for the example of an optical measuring apparatus 17, a detail aspect of the digital sensor signal processor 13. The analog input and output 13a comprises an analog controllable signal amplifier 34 which is followed by an analog signal line 21 by an analog-digital converter 35 with 16 bit resolution. The so produced digital signal is supplied via a digital signal line 22 to the central processor 13d. The photodetector 3 is connected via the analog signal line 21 to the signal amplifier 34. The amplification factor of the signal amplifier 34 can be controlled from the central processor 13d via the digital signal line 22. In order to ideally exploit the resolution capability of the analog-digital converter 35, a weak signal of the photodetector 3 is amplified in accordance with a rule preset by the software of the central processor 13d.

The optical measuring apparatus 17 shown in FIG. 5 for the pulse oximetric measurement of the oxygen saturation (SpO$_2$) measures the light transmitted through the finger 33 in that the two light emitting diodes 2a, 2b are arranged on the one side of the finger 33 and the photodetector 3 on the other side. The light emitting diodes 2a, 2b are connected via analog signal lines 21a, 21b to a switch over device 31 which in each case supplies one of the light emitting diodes 2a, 2b with power. The central processor 13d is connected via the digital signal line 22 to the digital-analog converter 36 (DAC) which generates an analog signal 21 for the control of the switch over device 31. Important components of the sensor signal processor 13 are thus the analog-digital converter 35 and also the digital-analog converter 36, thanks to which the measuring apparatus 17, which operates in analog manner, can be operated. A substantial advantage of the digital sensor signal processor 13 can be seen in the fact that the measuring apparatus 17 is controlled by the central processor 13d, i.e. by its software. A plurality of further measuring apparatuses or regulating systems, for example the electrochemical measuring apparatus 19 or the heating system 18, can be connected as illustrated to the digital sensor signal processor 13 in place of the optical measuring apparatus 17 shown by way of example in FIG. 5. It has proved particularly advantageous to use the sensor signal processor 13 in combination with the optical measuring apparatus 17 for the pulse oximetric measurement. It is known that the sensitivity of the pulse oximetric measurement is restricted in that interference signals and electronic noise are superimposed on the measurement signals. The sensor 1 of the invention converts the analog signal of the photodetector 3 with the aid of the sensor signal processor 13 within the sensor 1 into a digital signal. The analog signal line 21 is very short and is moreover screened against the outside by the metallic screen 16, so that the analog signal of the photodetector 3 is hardly impaired by interference signals or electronic noise. The digital signal can be supplied via the digital signal line 22 without loss of quality to the higher level signal evaluation device 37. It is known that the primary measuring signals, that is to say the measuring signals measured by the photodetector 3, can be very weak when using the pulse oximeter measurement. The sensor 1 of the invention enables interference signals and electronic noise to be largely avoided, so that measurements with weak primary measurement signals can also still be evaluated.

The arrangement shown in FIG. 5 is, for example, controlled by the central processor 13d in such a way that the photodetector 3 controls one after the other the light of the infrared light emitting diode 2a, the light of the red light emitting diode 2b and thereafter measures the light caused by the environment when none of the light emitting diodes 2a, 2b are energised. These three measured values are for example detected 4 times within 16 milliseconds and thereafter sent as a data packet comprising 12 values each having 16 bits, via the digital signal line 22 to the higher level signal evaluation device 37. Further values can also be transmitted in this data packet, such as the temperature or the measurement values of the electrochemical measuring apparatus 19.

In a further advantageous embodiment the signals measured by the measuring apparatus 17, 18, 19 are converted by the sensor signal processor 13 into a normalised digital output signal. For example the temperature measured in the sensor 1 with the temperature sensor 7 is normalised in such a way that the digital value 0 corresponds to the value 0° C. and the digital value 10000 corresponds to the value 100° C.

In order to further improve the accuracy of the measured values, the characteristic values of at least one of the electronic components used in the sensor 1, for example the characteristic of the photodetector 3, of the light emitting diodes 2a, 2b, or as shown in FIG. 7 the characteristic 52 of the temperature sensor 7, are stored in the sensor 1 in a further advantageous embodiment. The values of the characteristic 52 are preferably stored in the additional memory 23. The characteristic 52 can be stored in the most diverse manners, for example as a polygonal chain. The characteristic 52 shown in FIG. 7 is essentially a straight line, so that the parameters of the characteristic 52 are uniquely determined by the storage of the slope 53 and also of the offset 54. In this way the characteristics 52 of some or all important electronic components of the sensor 1 can be stored in the additional memory 23.

The storage of the characteristics 52 results in the following decisive advantages:

As a result of the manufacturing tolerances, each electronic component has an individual scatter, which results in an individual characteristic 52 for each electronic component. Since this individual characteristic 52 is stored in the sensor 1, the central processor 13d can access these values and can convert the measured analog signals in an extremely precise manner into normalised digital values. In place of the individual characteristics 52 only one characteristic 52 can, however, also be stored which has, for example, the same values for a series of components.

The measurement accuracy of the sensor is increased.

The sensor 1 need only be calibrated at relatively large time intervals. Moreover, the calibration is simplified. For example the electrode 4 has a characteristic with a constant slope dependent on the electrolyte 51. Since the electrolyte 51 dries out in the course of time, the offset of this characteristic, however, changes so that during calibration only the offset has to be newly determined, whereas the value of the slope does not have to be fed in anew.

An ageing of the electronic components, for example of the luminous power of the light emitting diodes can be automatically detected by the digital sensor signal processor 13 with the aid of the photodetector 3 and the age-dependent changed characteristic 52 can be stored in the additional memory 23 in place of the original characteristic 52.

The digital output values of each sensor 1 can be preset in a consistent manner. Thus, a defective sensor 1 can, for example, be replaced without problem. A calibration of the sensor, for example an adaptation to the higher level signal evaluation device 37 is not necessary.

Further data can be stored in the additional memory 23, for example an individual number for each sensor 1 or a designation for the type of the sensor 1, so that the higher level signal evaluation device 37 can automatically recognise the characteristics of the sensor 1. Patient data can also be stored in the additional memory 23, so that this data is immediately available to the memory of a new evaluation device 37 changing the sensor 1 by unplugging it. Data evaluated in the additional memory 23 could also be stored by the evaluation device 37, so that at least a part of the evaluated data are stored in the sensor 1. On changing the sensor 1 by plugging it into a further evaluation device 37, this evaluation device has available all the data stored in the sensor 1.

The sensor signal processor 13 can also include an operating hour counter with which the entire operating time of the sensor is detected. If the ageing behaviour of an electronic component, for example of the LED 2 is known, then the change of the characteristic which is to be expected can be corrected.

In a preferred method only the micro-pH-electrode 4 or the electrode 20 is periodically newly calibrated. Since the electrolyte 51 looses liquid in the course of time, the micro-pH-electrode 4 must be repeatedly newly calibrated. The respective new values determined with the aid, for example, of a calibrator, can be stored by the sensor signal processor 13 in the additional memory 23.

FIG. 6 shows schematically a block circuit diagram of a system for the measurement of physiological parameters. The sensor 1 is connected in signal conducting manner via the cable 44 with the higher level signal evaluation device 37. In place of the cable 44, a cableless connection could also be provided in that the digital information is, for example, transmitted by means of electromagnetic waves via a transmitter/receiver 44a. The one transmitter/receiver 44a can be arranged together with a battery in a housing 47. The sensor 1 has in this arrangement to be supplied with electrical energy from a non-illustrated energy source. The signal evaluation device 37 comprises essentially a digital sensor interface 38 and subsequently a computer 39 also termed a multi parameter processor. The computer 39 uses the software corresponding to the respective sensor 1 in order to evaluate the digital data. If the sensor 1, for example, has the optical measuring apparatus 17 shown in FIG. 5, then the computer 39 calculates from the measured values the oxygen saturation $SpO_2$ with the aid of algorithms known per se and additionally, if required, the pulse frequency. An input and output device 48 is arranged after the computer 39 with a controller 40 which controls the computer 39, a keyboard 41, a screen 42 and also a sound generator 43. The signal evaluation device 37 could also be arranged within the sensor 1.

The arrangement in accordance with FIG. 6 has the advantage that a single evaluation device 37 suffices in order to evaluate the measurement signals of different sensors 1. The signal evaluation device 37 must have different software programs available so that it can access the corresponding evaluation software depending on the sensor 1. The hardware of the signal evaluation device 37, however, remains identical. Since, in a preferred embodiment, the signal evaluation device 37 automatically recognises the type of the sensor 1, different sensors 1 can also be connected to the sensor interface 38 without problem, without additional adjustments being required. In a further embodiment two or even more sensors 1, 1a can also be connected to the same signal evaluation device 37.

FIG. 4 shows in a block circuit diagram a further embodiment of a sensor 1. The analog measurement values of the electrochemical measuring apparatus 19 or of the photodetector 3 are amplified in an impedance buffer 39 and are thereafter passed via the analog signal line 21 to the digital sensor signal processor 13. The measurement signal of the temperature sensor 7 is also supplied to it. The sensor signal processor 13 is connected via digital signal lines 22 to the additional memory 23, to the digital temperature sensor 7a, to the serial RS-232 interface 24 and also, if required, to a programming device 30. The serial interface 24 is connected via the serial digital signal line 22a to a cable connection device 32 from which the leads 26a, 26b, 27a, 27b are led in the form of a common cable to the signal evaluation device 37. The feed voltage 27a and the ground 27b are supplied as lines 27 to the amplifiers 31 and also to the sensor signal processor 13. The sensor signal processor 13 controls the amplifier 31 via the analog signal lines 21 and thus the two-colour light emitting diode 2 and also the electrical resistor 6.

In the illustrated embodiment the cable includes four conductors 26a, 26b, 27a, 27b. This cable can be made very thin and flexible which gives the advantage that a movement of the cable has no effect or hardly any effect on the position of the sensor 1. Bidirectional digital data can also be exchanged via a single conductor 26a, so that one cable comprising the conductors 26a, 27a and 27b is sufficient for the operation of the sensor 1. A cable of this kind can be made particularly thin and flexible.

FIG. 8 shows in a longitudinal section a further embodiment of a sensor 1 which is clipped with the aid of a clip 58 with a light reflecting surface 58a to an earlobe 57. In distinction to the embodiment shown in FIG. 1, the electrochemical measuring apparatus 19 is formed as a semiconductor which permits the carbon dioxide to be measured directly and without an electrolyte 51. The measuring apparatus 19 could also be designed as a solid state electrode without an internal liquid electrolyte. The measuring apparatus 19 could also be designed as a semiconductor, for example in thick film technology, with a pH-sensitive layer. The sensor 1 shown in FIG. 8 has a housing 9 comprising first and second part housings 9a, 9b. The measured signals are led away via a connection means 26 formed as a cable.

FIG. 9 shows in a longitudinal section a further embodiment of a sensor. In distinction to the embodiment shown in FIG. 1, the circuit board 10 has two flexible sections 10a which is provided with conductive tracks. A preamplifier 12a is arranged at the end of the one flexible section 10a and is connected to the inner conductor 4a. This arrangement permits the high ohmic and thus disturbance-sensitive signal of the inner conductor 4a to be amplified with the preamplifier 12a close to the output point. This enables a connection between the electrode 4 and the circuit board 10 which conducts a disturbance-free signal. The flexible section 10a enables a cost favourable manufacture of the sensor in that the circuit board 10 is equipped with the electronic components 2, 3, 6, 7, 12, 13, the electrochemical measuring apparatus 19 is then bonded to the circuit board 10, the preamplifier 12a is contacted with the inner conductor 4a and then the space bounded by the second housing part 9b and the circuit board 10 is potted with an electrically highly insulating epoxy resin. On the other flexible section 10a there is arranged a contact point 11 and also a cable 26 leading to the outside. The clamping ring 55 with membrane 50 which is only indicated in FIG. 1 is moreover shown in FIG. 9 and is releasably connected to the sensor 1 via a snap device 56.

FIG. 11 shows a longitudinal section through a sensor 1 designed as a respiratory gas measuring apparatus 60. In the interior of the tubular housing 60a there are arranged, in addition to further non-illustrated components, a measuring apparatus 19, a temperature sensor 7, a moisture sensor 62 and also a digital sensor signal processor 13. In the embodiment shown in FIG. 12 the measuring apparatus 19 consists of the two components light emitting diodes 2 and photodetector 3. This measuring apparatus 19 could also be designed as semiconductor chip which permits light of different wavelength to be produced and/or measured in order to measure a spectrum and determine different gas proportions in the respiratory gas.

What is claimed is:

1. A sensor for the measurement of physiological parameters comprising at least one measuring apparatus; a digital sensor signal processor which is arranged in the sensor and which is connected in a signal conducting manner to the measuring apparatus and which makes available a digital output signal; and a cable enabling an exchange of data with a subsequent device, the cable enabling electrical energy to be supplied into the sensor.

2. A sensor in accordance with claim 1, comprising at least one measuring apparatus selected from the group consisting of a measuring apparatus to measure $CO_2$ content;
a measuring apparatus to measure $O_2$ content;
an optical measuring apparatus to measure pulse oximetric measurement of arterial oxygen saturation;

a measuring apparatus to measure pulse frequency;
a measuring apparatus to measure hematocrit (HCT);
a measuring apparatus to measure the blood pressure (CNIBP);
a measuring apparatus to measure components of the respiratory gas;
a measuring apparatus to measure the body temperatures; and
a measuring apparatus to measure the moisture content.

3. A sensor in accordance with claim 1, wherein the measuring apparatus includes an electrochemical measuring apparatus.

4. A sensor in accordance with claim 1, wherein the measuring apparatus includes a semiconductor chip wherein the semiconductor chip permits the measurement of the concentration of a gas or of a gas mixture.

5. A sensor in accordance with claim 1, wherein the measuring apparatus includes an optical measuring apparatus comprising a light source and a photodetector.

6. A sensor in accordance with claim 5, wherein the measuring apparatus includes a semiconductor chip which permits at least one of the generation or measurement of light of different wavelengths.

7. A sensor in accordance with claim 1, comprising an electrical heating apparatus and a temperature sensor.

8. A sensor in accordance with claim 1, comprising a data memory to store data selected from one or more of the group consisting of a characteristic of the at least one measuring apparatus, measured values, and patient data.

9. A sensor in accordance with claim 1, comprising a signal transmitter functionally connected to a subsequent device wherein the signal transmitter includes a two pole cable.

10. A sensor in accordance with claim 1, comprising an at least partly rigid circuit board which is equipped with electronic components.

11. A sensor in accordance with claim 10, wherein the circuit board is equipped with an electrode.

12. A sensor in accordance with claim 11, wherein the electrode has a longitudinal direction (L); the circuit board is arranged extending substantially perpendicular to this longitudinal direction (L), and the circuit board is arranged within the length of the electrode.

13. A sensor in accordance with claim 10, wherein the circuit board includes a flexible section.

14. A sensor in accordance with claim 13, comprising a preamplifier arranged in the flexible section, the preamplifier being connected in a signal-conducting manner to an inner electrical conductor of the electrode.

15. A sensor in accordance with claim 10, wherein a substantially full area of an electrically conducting layer is arranged at the surface of or within the circuit board and is connected to ground.

16. A sensor in accordance with claim 10, wherein the circuit board has an aperture and an electrochemical measuring apparatus is arranged extending through the aperture.

17. A sensor in accordance with claim 10, wherein electronic components sensitive to disturbance are arranged on the circuit board separated from the remaining electronic components.

18. A sensor in accordance with claim 10, wherein the space between the circuit board and the sensor surface has a heat conducting medium, with the heat conducting medium being cast in place.

19. A sensor in accordance with claim 10, wherein the circuit board assembly is surrounded at least partly by a metallic layer.

20. A system for the measurement of physiological parameters comprising a sensor in accordance with claim 1, and a signal evaluation device, the signal evaluation device comprising a digital sensor interface and a processor.

21. A system in accordance with claim 20, wherein the digital sensor interface enables a digital signal transmitting connection to the sensor, with the digital sensor interface being arranged after the processor and with the signal evaluation device being suited for the evaluation of the signals of different sensors through a corresponding choice of processor software.

22. A sensor in accordance with claim 1, comprising an electrical heating apparatus and a temperature sensor, the digital sensor signal processor being connected in a signal conducting manner to the electrical heating apparatus and the temperature sensor, whereby the digital sensor signal processor controls the temperature generated by the electrical heating apparatus.

23. A sensor in accordance with claim 1, wherein the sensor is adapted to be arranged on an earlobe, comprising a measuring apparatus for the measurement of oxygen and a measuring apparatus for the measurement of carbon dioxide in the blood.

24. A sensor in accordance with claim 23, the measuring apparatus being adapted to measure arterial oxygen saturation, and the measuring apparatus being adapted to measure transcutaneous carbon dioxide partial pressure.

25. A sensor in accordance with claim 1, comprising a planar surface, the surface comprising a heat conducting potting forming at least part of the planar surface, the heat conducting potting being arranged so that the heat produced by the electrical heating apparatus is transferred to the sensor surface.

26. A sensor in accordance with claim 1, comprising a clip to connect the sensor to an earlobe.

27. A method for the measurement of physiological parameters comprising: detecting an analog measured value of a measuring apparatus by a sensor, converting the analog measured value into digital values in the sensor, by a digital sensor signal processor, supplying the digital values using a connection cable to a subsequent device and supplying power for the sensor via the connection cable.

28. The method in accordance with claim 27, comprising: storing reference data of the measuring apparatus in the sensor, compensating the digital values corresponding to the reference data and supplying the so compensated digital values to the subsequent device.

29. The method in accordance with claim 27, comprising calculating a corresponding physiological parameter from the digital values, using a processor arranged in the subsequent device.

30. The method in accordance with claim 27, wherein patient data is stored in a memory of the sensor.

31. The method in accordance with claim 27, wherein at least parts of the values of the physiological parameters calculated in the subsequent device are stored in a memory of the sensor.

32. The method in accordance with claim 31, comprising connecting the sensor with a plurality of subsequent devices one after the other, and in that at least a part of the values calculated in the respective subsequent devices are stored in a memory of the sensor.

33. The method in accordance with claim 32, wherein the subsequent devices are respectively connected to the sensor, taking over at least a part of the data stored in the memory of the sensor.

34. The method in accordance with claim 27, wherein the sensor is arranged on the ear.

35. The method in accordance with claim 27, wherein the digital output is transferred over a connection cable to a subsequent device using a bi-directional exchange of digital date.

36. The method in accordance with claim 27, comprising heating the sensor, measuring the temperature of the sensor, and controlling the heat generation and the temperature, to maintain a sensor surface at a constant temperature.

37. The method in accordance with claim 36, wherein the temperature is measured by a digital temperature sensor and an analog temperature sensor, the method comprising comparing the measurements from the digital temperature sensor and analog temperature sensor, and, if a relatively greater deviation is detected, concluding that at least one of the temperature sensors is defective.

38. A method for measuring blood substances at the earlobe, the method comprising:

attaching a sensor to an earlobe;

accepting power to the sensor from a connection cable to a subsequent device;

measuring values of physiological parameters in the blood;

converting, in the sensor, the values to digital values; and transmitting a digital output over the connection cable to a subsequent device.

39. The method of claim 38, comprising accepting data at the sensor via the connection cable.

40. The method of claim 38, comprising heating the sensor.

41. The method of claim 40, comprising controlling the heating by a processor contained within the sensor.

* * * * *